(12) United States Patent
Falk et al.

(10) Patent No.: US 6,454,548 B2
(45) Date of Patent: Sep. 24, 2002

(54) LOW POWER ELECTROMAGNETIC PUMP

(75) Inventors: Theodore J. Falk; Norbert W. Frenz, Jr., both of Clarence, NY (US)

(73) Assignee: Wilson Greatbatch Ltd., Clarence, NY (US)

( * ) Notice: Subject to any disclaimer, the term of this patent is extended or adjusted under 35 U.S.C. 154(b) by 0 days.

(21) Appl. No.: 09/911,566

(22) Filed: Jul. 24, 2001

Related U.S. Application Data

(63) Continuation of application No. 09/099,838, filed on Jun. 18, 1998, now Pat. No. 6,264,439.

(51) Int. Cl.⁷ ................................................. F04B 17/04
(52) U.S. Cl. ...................... 417/417; 417/254; 310/15; 310/23; 310/45; 92/130 R; 92/135; 29/602.1
(58) Field of Search ................... 417/417, 254, 417/559, 569, 570; 310/15, 23, 45; 92/130 R, 135; 29/602.1

(56) References Cited

U.S. PATENT DOCUMENTS

| | | | |
|---|---|---|---|
| 4,636,150 A | * | 1/1987 | Falk et al. ................... 417/417 |
| 5,695,827 A | * | 12/1997 | Shalaby ...................... 427/528 |
| 5,771,873 A | * | 6/1998 | Potter et al. ................. 123/688 |
| 5,800,139 A | * | 9/1998 | Yamada ...................... 417/417 |
| 5,915,929 A | | 6/1999 | Falk et al. |

* cited by examiner

Primary Examiner—Charles G. Freay
Assistant Examiner—W Rodriguez
(74) Attorney, Agent, or Firm—Hodgson Russ LLP

(57) ABSTRACT

An electromagnetic pump including a housing having an interior fluid containing region, a check valve operatively flow in a direction from an inlet toward an outlet and blocking fluid flow in a direction from the outlet to the inlet, an electromagnet carried by the housing located external to the fluid containing region, and a barrier of fluid impervious material for isolating the electromagnet from the fluid. An armature movable in the housing through pumping and return strokes has a pole portion located for magnetic attraction by the electromagnet and has a plunger portion extending from the pole portion. The armature plunger and pole portions have formations crimped together to secure the plunger and pole portions together. The barrier or an end surface of the armature pole portion are shaped to enhance separation of the barrier and armature pole portion at the beginning of the return stroke. The housing is provided with shims for adjustment of the delivered stroke volume.

9 Claims, 11 Drawing Sheets

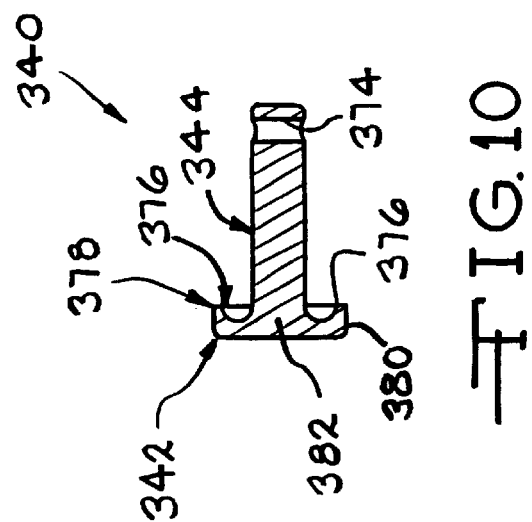
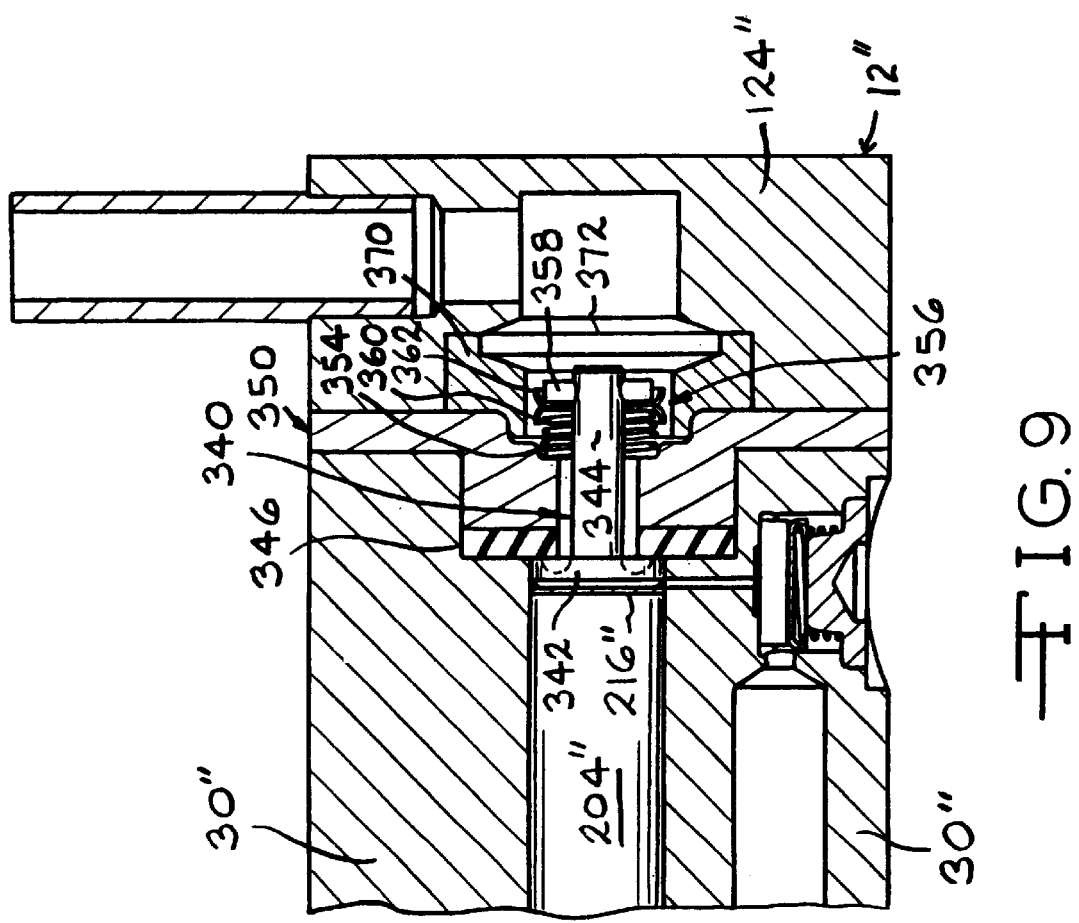

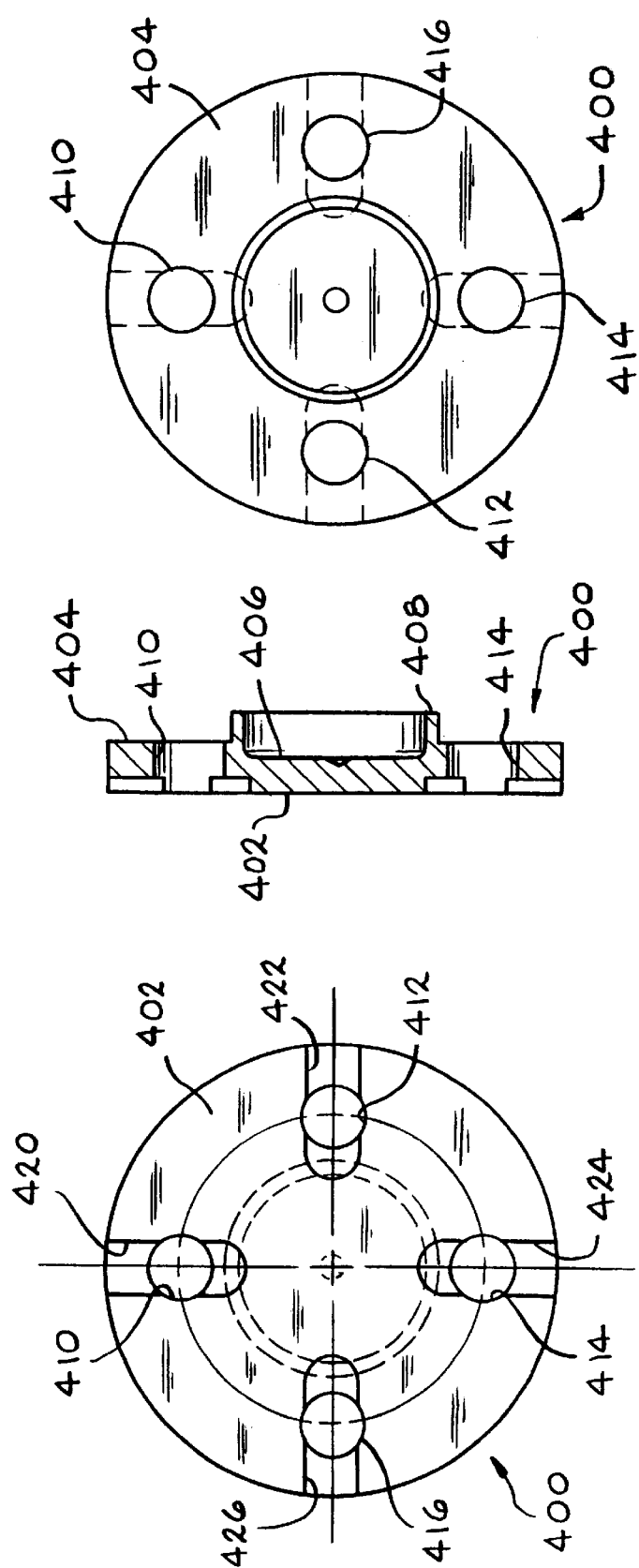

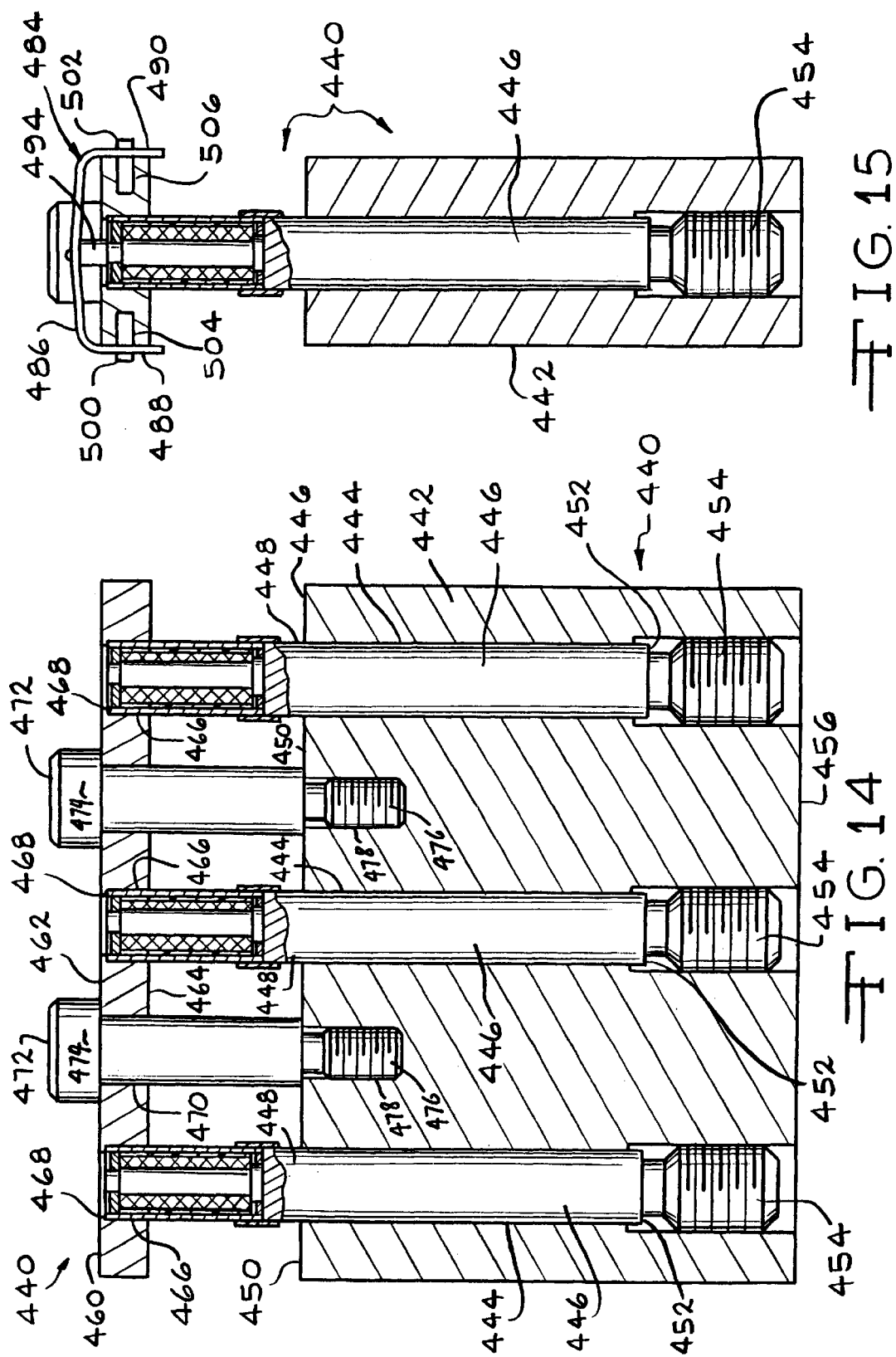

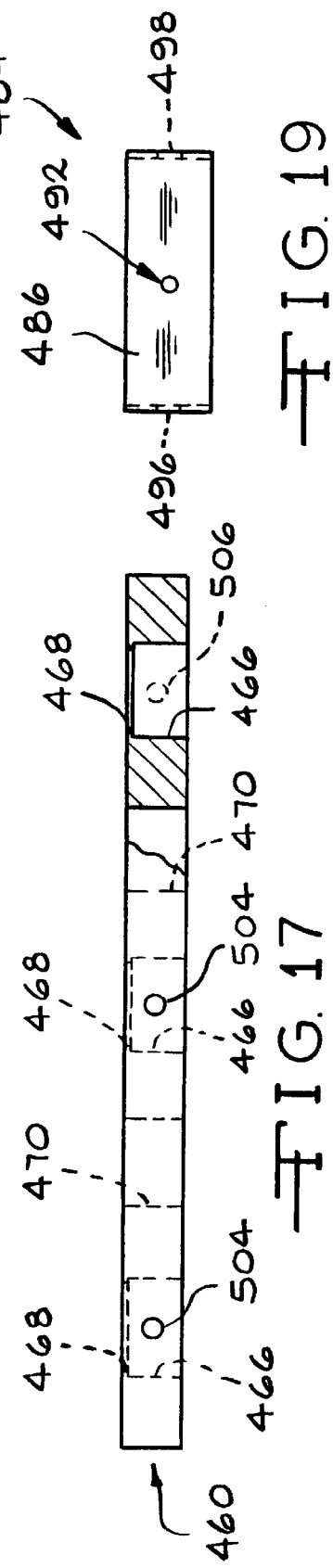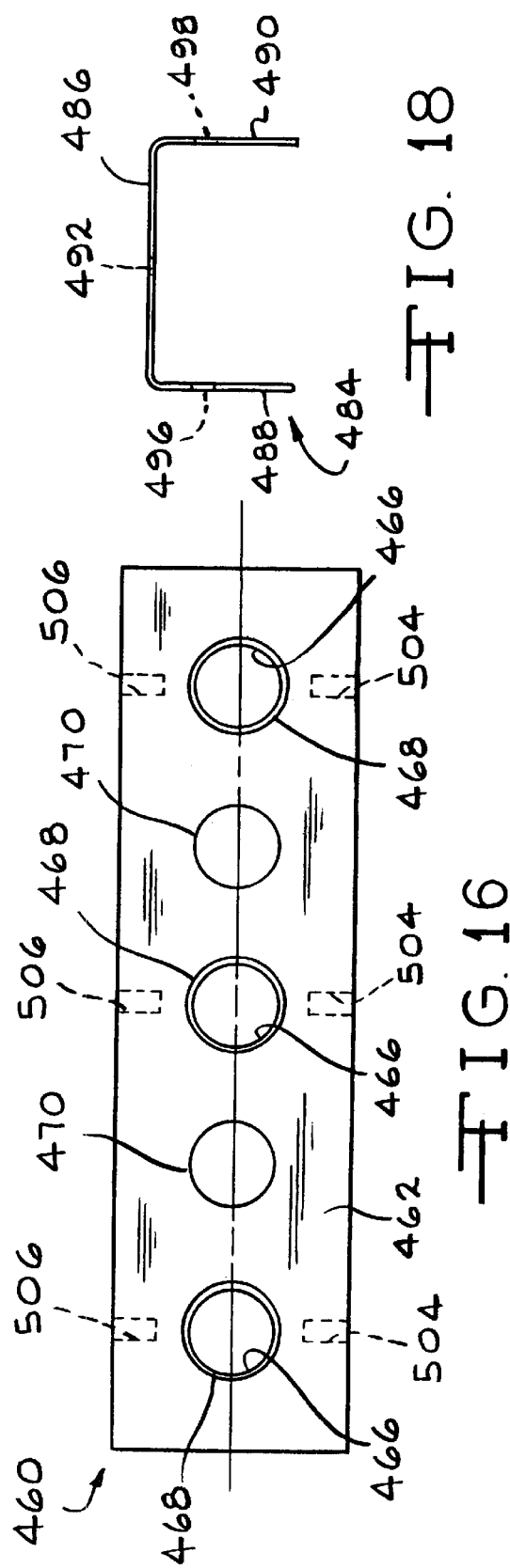

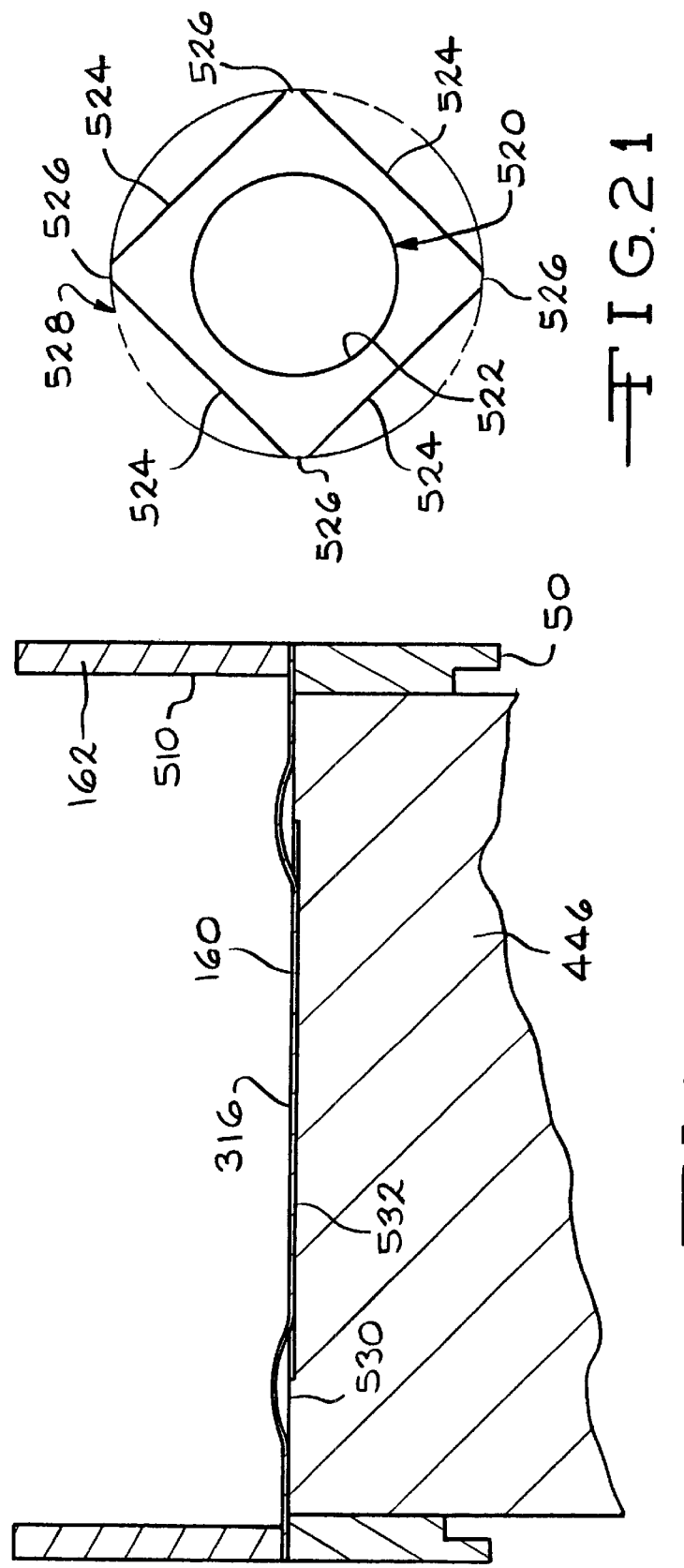

LOW POWER ELECTROMAGNETIC PUMP

This is a continuation of Ser. No. 09/099,838 now U.S. Pat. No. 6,264,439 filed on Jun. 18, 1998.

BACKGROUND OF THE INVENTION

This invention relates to the art of electromagnetically operated fluid pumps, and more particularly to a new and improved electromagnetic pump which operates at extremely low power.

One area of use of the present invention is implantable drug delivery systems, although the principles of the present invention can be variously applied. The principal requirements for a pump in such applications are low power drain, since the pump must be driven by an implanted battery, and compatibility with the drug being pumped. Additional important requirements are that the pump have a simplified structure and method of assembly while at the same time having improved performance, that the pump operates in a manner preventing damage to fragile drugs such as insulin, that moving parts of the pump be resistant to wear and that the stroke volume of the pump be adjustable within a relatively short time.

It would, therefore, be highly desirable to provide an electromagnetically operated pump which is safe, reliable, small in size, light in weight, which operates without excessive demand on the available energy supply, which is compatible with drugs or similar liquids to be pumped, which has a relatively simple structure and method of assembly while at the same time having improved performance, which operates in a manner preventing damage to fragile drugs such as insulin, which has wear resistant movable parts and which has a relatively quickly adjustable stroke volume.

SUMMARY OF THE INVENTION

It is, therefore, a primary object of this invention to provide a new and improved electromagnetically operated pump.

It is a more particular object of this invention to provide such a pump which operates at extremely low power levels.

It is a further object of this invention to provide such a pump which is compatible with the fluid being pumped.

It is further object of this invention to provide such a pump which is electronically and magnetically efficient.

It is a further object of this invention to provide such a pump which operates in a manner preventing damage to fragile liquids such as insulin.

It is a further object of this invention to provide such a pump wherein the stroke volume is adjustable within a relatively short period of time.

It is a further object of this invention to provide such a pump wherein the moving parts are resistant to wear;

It is a further object of this invention to provide such a pump which has a relatively simple structure and method of assembly.

The present invention provides an electromagnetic pump comprising a housing having an interior fluid containing region including a fluid receiving chamber in communication with an inlet, a fluid output chamber in fluid communication with an outlet, check valve means operatively associated with the fluid containing region for allowing fluid flow in a direction from the inlet toward the outlet and blocking fluid flow in a direction from the outlet to the inlet, electromagnet means carried by the housing located external to the fluid containing region, and barrier means of fluid impervious material for isolating the electromagnet means from the fluid chambers. An armature movable in the housing has a pole portion located for magnetic attraction by the electromagnet means and has a plunger portion extending from the pole portion, the armature being movably supported in the housing for movement from a rest position through a forward pumping stroke when attracted by the electromagnet to force fluid from the output chamber through the outlet and for movement in an opposite direction through a return stroke back to the rest position. There also is provided means defining a magnetic circuit including the electromagnet means, the armature and a gap between the armature pole portion and the electromagnet means for moving the armature toward the electromagnet means to close the gap in response to electrical energization of the electromagnet means.

The foregoing and additional advantages and characterizing features of the present invention will become clearly apparent upon a reading of the ensuing detailed description together with the included drawing wherein:

BRIEF DESCRIPTION OF THE DRAWING FIGURES

FIG. 9 is a fragmentary sectional view of a pump similar to the pump of FIG. 1 and provided with an improved inlet check valve;

FIG. 10 is a longitudinal sectional view of the check valve element in the pump of FIG. 9;

FIG. 11 is an elevational view of an armature pole portion according to another embodiment of the present invention;

FIG. 12 is a sectional view of the armature pole portion of FIG. 11;

FIG. 13 is an elevational view of the opposite end of the pole portion of FIG. 11;

FIG. 14 is a longitudinal sectional view with parts removed of a fixture assembly for carrying out the method of the present invention;

FIG. 15 is a lateral sectional view of the fixture assembly of FIG. 14 and showing the clamping means thereof;

FIG. 16 is a top plan view of the clamp member of the fixture of FIGS. 14 and 15;

FIG. 17 is a side elevational view thereof, partly in section;

FIG. 18 is a side elevational view of the clamping means of the fixture of FIGS. 14 and 15;

FIG. 19 is a top plan view thereof;

FIG. 20 is a fragmentary sectional view illustrating an aspect of the present invention; and FIG. 21 is a plan view of a centering spacer used in the method of the present invention.

DETAILED DESCRIPTION OF THE ILLUSTRATED EMBODIMENTS

Figure 1A:
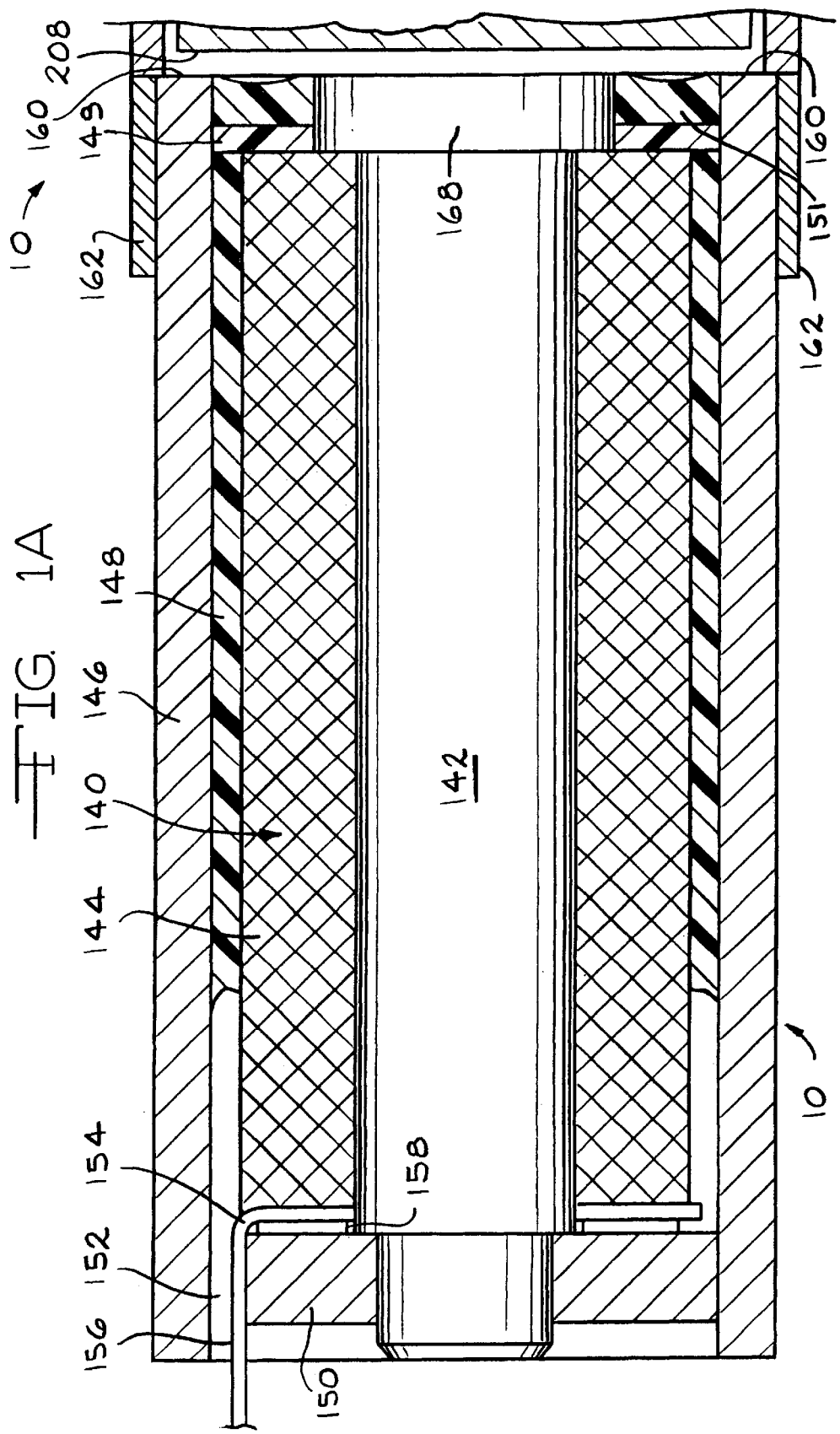
FIG. 1 is a longitudinal sectional view of a pump according to one embodiment of the present invention.
Figure 1B:
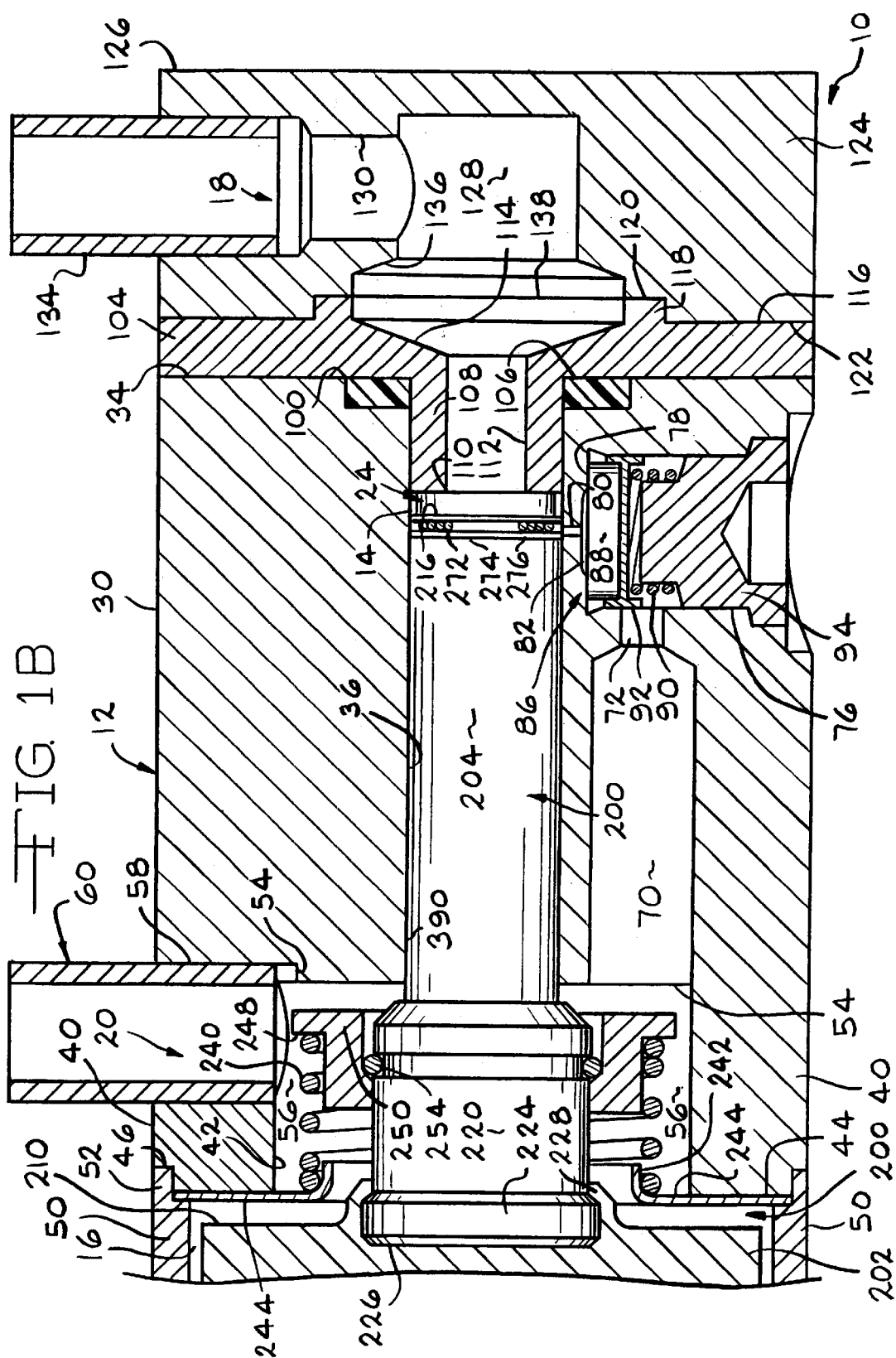

Referring now to FIG. 1, a pump 10 according to one embodiment of the present invention includes a housing 12 which is generally hollow, either rectangular or cylindrical in overall shape, and pump 10 includes an interior region for containing fluid, i.e. the liquid to be pumped. The hollow interior region includes a fluid receiving chamber 14 and a fluid output chamber 16 in fluid communication therewith which will be described in further detail presently. There is an inlet port generally designated 18 in fluid communication with the fluid receiving chamber 14 and adapted to be connected in the fluid handling circuit containing pump 10. There is also an outlet port 20 in fluid communication with the fluid output chamber 16 and adapted to be connected in the fluid handling circuit. In the illustrative pump shown, inlet port 18 is adapted to be connected to a source or supply of fluid to be pumped, and outlet port 20 is adapted to be in fluid communication with a location to which fluid is to be pumped. There is also provided check valve means generally designated 24 operatively associated with the fluid containing region of pump 10 for allowing fluid flow in a direction from the inlet 18 through outlet 20 and blocking fluid flow in a direction from the outlet through the inlet. In the pump of this embodiment, check valve means 24 is within the pump and associated with the pump armature in a manner which will be described.

Housing 12 is generally hollow including a first body portion 30 of relatively substantial wall thickness and terminates at one end, i.e. the right-hand end as viewed in FIG. 1, in an axial end face 34. Housing portion 30 defines an interior region of constant diameter having an inner surface 36. Housing 12 includes a second body portion 40 extending from portion 30 and which defines an interior region of constant diameter having an inner surface 42. Body portion 40 terminates at the left-hand end as viewed in FIG. 1 in an axial end face 44. The outer surfaces of body portions 30 and 40 are of substantially equal cross-sectional shapes and dimensions so as to be substantially flush.

The junction between the end face 44 and outer surface of body portion 40 meet in an annular shoulder 46. The shoulder 46 receives one end of a first weld ring element 50 having an outer diameter substantially equal to the outer diameters of the cylindrical body portion 40 so as to be substantially flush therewith. Ring element 50 has a corresponding shoulder 52 at the one end thereof, i.e. the right-hand end as viewed in FIG. 1, and is welded to housing portion 40 at the shoulder 46 in a suitable manner. Ring 50 is joined at the opposite end thereof to other components of the pump housing in a manner which will be described.

Output chamber 16 is placed in fluid communication with outlet port 20 in the following manner. The inner surface 42 of housing body portion 40 and a wall portion 54 of housing body portion 30 define an open region 56 which is in fluid communication with output chamber 16. Housing portion 40 is provided with a radially extending bore or passage 58 into which is fitted one end of a conduit or fitting 60 which comprises a portion of the afore-mentioned fluid circuit and which will be described in further detail presently.

Thus, output chamber 16 is placed in fluid communication with outlet port 20 via the combination of region 56 and passage 58. Chamber 16 is placed in fluid communication with fluid receiving chamber 14 in the following manner. An axially extending passage 70 is provided in the body of housing portion 30, extending axially inwardly from wall portion 54 and which necks down to a smaller diameter short passage 72 at the opposite end thereof. Body portion 30 also is provided with a radially extending bore or passage 76 which extends inwardly from the outer surface thereof and terminates in a wall portion or surface 78 spaced outwardly from the inner surface 36. An orifice 80 places passage 76 in fluid communication with the interior region within inner surface 36. A recess 82 in surface 78 provides a transition between passage 76 and orifice 80. As will be described in detail presently, flow between passage 76 and orifice 80 is controlled by a bypass check valve 86 comprising a disc-shaped body or seat 88 having one surface contacting wall portion 78 and a biasing spring 90 having one end received in a cup shaped spring retainer 92 on the opposite surface of seat 88 and the other end fitted on the end of a plug 94 secured in passage 76.

Inlet port 18 is provided by the following arrangement. At the junction of end face 34 and inner surface 36 of housing portion there is provided an annular shoulder which receives a sealing ring 100. There is provided a ferrule element 104 having a disc-shaped body portion which contacts housing end face 34 and which has an outer diameter or dimension sized to be flush with the outer surface of housing portion 30. Ferrule 104 has an inner axial end face 106 provided with a central, hub-like axial extension 108 having an axial end face provided with an annular valve formation 110 which is shaped to define a sharp annular edge facing axially into the housing interior region. A central bore or passage 112 of constant diameter extends axially inwardly from valve formation 110 whereupon it meets a passage 114 of increasing diameter. Ferrule 104 also has an outer axial end face 116 provided with a central annual formation 118 which extends axially outwardly from end face 116 for a short distance. Formation 118 is received in a circular recess 120 formed in end an face 122 of an inlet body 124 having an opposite end face 126 at the right-handed end of pump 10 as viewed in FIG. 1 and having a diameter or outer dimension sized to be flush with the outer surfaces of ferrule 104 and housing portion 30. Inlet body 124 has a central chamber 128 in fluid communication with passage 114 and from which a radially disposed passage 130 extends into which is fitted one end of a conduit or fitting 134 which comprises a portion of the afore-mentioned fluid circuit and which will be described in further detail presently. Chamber 128 has an end portion 136 of increasing diameter substantially corresponding to passage 114 of ferrule 104. Thus, a flow path is defined through the central chamber of inlet body 124 and the passage portions 112 and 114 thereby defining inlet port 18. A disc-shaped filter element 138, preferably of the etched titanium type, is fitted between ferrule element 104 and inlet body 124 as shown in FIG. 1 so as to be in the flow path.

The pump of the present invention further comprises electromagnet means generally designated 140 carried by housing 12 and located external to the fluid containing region of the housing. As shown in FIG. 1 the electromagnet 140 includes a core 142 in the form of a spool which is generally solid cylindrical in shape. A coil 144 is wound on spool 142 and contained within a hollow housing 146 generally cylindrical in shape. A sleeve-like body 148 of encapsulant or potting material such as epoxy is between coil 144 and housing 146 and extends axially inwardly around the end of coil 144 facing housing 12. An annular spacer element 148 is located between the end of coil 144 and potting material 148 for a purpose to be described. One end of electromagnet 140 is adjacent and in abutting relation to housing 12 and the opposite end, i.e. the left-hand end as viewed in FIG. 1, is closed by an arrangement including a washer 150 and a body 152 of encapsulant or potting compound. Electrical connection from a power source, such as a lithium battery charging circuit and capacitor, to electromagnet 140 is provided via a conductor having a right-shaped body portion 154 soldered to coil 144 and a lead portion 156 extending axially outwardly from electromagnet 140. A washer shaped insulator 158 is provided between the conductor portion 154 and washer 150. Electromagnet 140 is joined to housing 12 in the following manner.

The interior, fluid containing region of housing 12 and the electromagnet 140 are separated by a barrier means of fluid impervious material in the form of a relatively thin plate or diaphragm-like component 160. A second weld ring 162 is provided on the end of magnet housing 146 adjacent pump housing 12. The outer diameter of ring 162 is substantially equal to the outer diameter of the first weld ring 50 so that the respective outer surfaces are substantially flush. The region between coil 144 and barrier 160 is occupied by an annular ring-like portion of the encapsulant 148. The housing and electromagnet structures are placed in abutting relation on opposite sides of the plate 160, and the assembly is secured together by a weld joining the respective outer surfaces of the weld rings 50 and 162. In addition, an enlarged annular end portion 168 of spool 142 contacts the central portion of plate 160 in a manner supporting the same.

The pump according to the present invention further comprises an armature generally designated 200 positioned in the fluid containing region of housing 12. The armature has a pole portion 202 located for magnetic attraction by the electromagnet 130 and a plunger portion 204 extending from the pole portion 202. The armature pole portion 202 is located for movement within chamber 16 as shown in FIG. 1. The armature 200 is movably supported in housing 12 for movement from a rest position through a forward pumping stroke when attracted by the electromagnet 140 to force fluid out through outlet 20, and for movement in an opposite direction through a return stroke back to the rest position. In FIG. 1, armature 200 is shown at an intermediate position during the forward pumping stroke.

Armature pole portion 202 occupies a major portion of chamber 16 in which it is located, is in the general form of a disc, and has a lateral dimension as viewed in FIG. 1 which is several times greater than the longitudinal dimension thereof. Pole portion 202 comprises a solid, monolithic body of magnetic material having a first axial end face 208 which faces toward barrier means 160 and a second, opposite axial end face 210 which faces toward inlet port 18. Thus end faces 208, 210 are disposed substantially perpendicular to the direction of travel of armature 200.

Pole portion 202 is exclusively of magnetic material, preferably a chrome-molybdenum-iron alloy which is heat treated. Examples are 29-4 and 29-4C chrome-molybdenum iron alloy. This alloy has high corrosion resistance, and has adequate magnetic characteristics for use in pump 10 when heat treated. In other words, the alloy is heat treated to provide a BH characteristic for the alloy which yields the requisite level of magnetic flux density and coercive force. Furthermore, the alloy is sufficiently resistant to corrosive effects of insulin stabilized for use in implantable drug delivery systems as well as other corrosive drugs.

In particular, the afore-mentioned chrome-molybdenum-iron alloy is a ferritic stainless steel alloy containing 29% chromium, 4% molybdenum and the remainder substantially iron. The afore-mentioned heat treatment involves an anneal and rapid cool of the armature pole portion 202. In particular the procedure involves a short magnetic anneal at a temperature above that which can form a harmful second phase in the alloy followed by cooling rapidly enough to avoid second phase formation but not so rapidly as to degrade magnetic properties. Heating of armature pole portions 202 of 29-4 alloy is performed for example in a clamshell furnace at a temperature of about 1010° C. for about twenty minutes whereupon the parts 202 are removed quickly to the ambient in a manner allowing complete cooling for a minimum of 25 minutes. The cooling rate during the first portion of the cooling cycle from 1010° C. down to black, i.e. down to 600° C., should be maintained at about 60 seconds.

Thus, the armature pole portion 202 terminates at the end facing electromagnet 140 in an axial end face which serves as the pole face and is disposed substantially perpendicular to the armature axis. The armature pole face together with electromagnet 140 define the magnetic circuit gap which is closed during the forward armature stroke. The pole face is of relatively large cross-sectional area as compared to the cross sectional area of the armature plunger portion 204.

The armature 200 includes a plunger portion 204 which is movably positioned within the interior region of housing portion 30 and extends axially from armature pole portion 202 toward inlet 18. Plunger 204 is substantially cylindrical in shape having an outer diameter slightly less than the diameter of the interior passage in housing portion 30 to allow reciprocal movement of plunger 204 within housing portion 30 during the forward and return strokes of armature 200. Plunger 204 terminates in an axial end face 216 which faces toward inlet 18.

The armature pole and plunger portions 202 and 204, respectively, are joined together in the following manner. Plunger 204 has an enlarged, generally cylindrical formation 220 on the end adjacent pole portion 202 and which formation has a diameter slightly greater than that of plunger 204. At the end of formation 220 adjacent pole portion 202 there is provided an annular head or enlargement 224. The end face 210 of pole portion 202 is provided with a recess 226 bordered by an annular peripheral flange 228. Recess 226 is of a diameter sized to receive the outer end of bead 224, and flange 228 is of a size such that it can be crimped onto and over formation 224 as shown in FIG. 1 thereby providing a tight and secure connection between the end of armature plunger portion 204 and the armature pole portion 202.

There is provided biasing means in the form of a coil spring 240 for urging or returning armature 200 toward the rest position in a manner which will be described. One end of return spring 240 seats in an annular shoulder 242 of a first spring retainer 244 in the form of a relatively thin, washer-like element of metal which is fixed at the outer annular periphery thereof in the junction between weld ring 50 and housing portion 40. The central opening in retainer 244 is of a diameter larger than that of plunger formation 220 and head 224 and is generally concentric therewith. The opposite end of return spring 240 seats in an annular shoulder 248 on the outer surface of a second spring retainer element 250 which is removably mounted on plunger enlargement 220 in a manner which will be described. Retainer element 250 is in the general form of a sleeve having an outer diameter sized to accommodate return spring 240 as shown in FIG. 1 and provided with an annular rim or flange which provides the shoulder 248. The inner diameter of element 250 is sized to enable it to fit on the plunger enlargement 220. A locking ring 254 seated in an annular groove in formation 220 engages an inner annular shoulder on element 250 enabling the element to be removably retained on formation 220 in a manner which will be described.

The pump according to the present embodiment includes check valve means 24 operatively coupled to the armature 200 and located in the fluid-receiving region of the housing for opening and closing the pump inlet. In particular, the check valve means 24 comprises a valve member positioned and biased for closing the pump inlet when the armature is in the rest position and allowing opening of the inlet after the armature begins movement associated with the forward pumping stroke. In the embodiment of FIG. 1, check valve means 24 is located in the fluid-receiving chamber 14 between inlet 18 and the armature plunger end face 216. Check valve means 24 includes a body or seat 270 in the form of a disc having a surface facing and adapted to sealingly contact the edge of the valve formation 110, a backing element or plate 272 contacting disc 270, a shim 274 contacting armature end face 216, and a biasing spring 276 in the form of a conical spring between backing element 272 and shim 274. The valve seat 270 is loosely positioned in the passage and is relatively thin. As a result, seat swelling caused by temperature changes or the presence of various liquids has a smaller effect on the liquid volume delivered per stroke. This seat structure makes it possible to reduce the clearance between seat 270 and the passage in housing portion 30. The small clearance and thinner seat 270 together contribute significantly to reducing the volume of the fluid-receiving chamber 14 with armature 200 in the rest position. The backing element 272 provides a bearing surface for spring 276 at all times and when armature 200 is at rest. The biasing spring is compressed to an approximately flat configuration when armature 200 is in the rest position.

In operation, inlet 18 is connected via conduit 134 to a source or supply of fluid to be pumped, and outlet 20 is connected via conduit 60 to a point or location of use for the pumped fluid. The armature 200 is moved through a forward pumping stroke in response to electrical energization of electromagnet 140. One way of energizing magnet 140 is to charge a capacitor from a battery and then discharge that capacitor through coil 144. Other procedures can of course be employed for electrically energizing coil 144 in a known manner. Prior to electrical energization of magnet 130, armature 200 is in a rest position where the check valve 24 is located with the surface of body 270 seated against the edge of valve formation 110 surrounding the opening of the inlet fitting passage to block fluid communication from inlet 18 to the fluid receiving chamber 14. In the rest position of armature 200, pole portion 202 is spaced from diaphragm 160 thereby defining the gap in the magnetic circuit. In the rest position, this gap between pole portion 202 and diaphragm 160 is of maximum length.

When coil 144 is electrically energized, the armature pole portion 202 is attracted toward magnet 140 thereby causing armature 200 to be drawn toward diaphragm 160. Electromagnetic flux travels through the magnetic circuit including the electromagnet core 142, washer 150, magnet housing 146, the included portion of the periphery of diaphragm 160 between the end face of housing 146 and end face 208 of armature pole body 202, armature pole body 202 and the gap between the armature pole face 208 and diaphragm 160. As armature 200 is moved in the forward pumping stroke, i.e. in a direction to the left as viewed in FIG. 1, the armature pole body 202 moves further toward diaphragm 160 thereby decreasing the gap in the magnetic circuit. During the forward pumping stroke of armature 200 fluid is forced out through region 56 and passage 58 through the outlet 20 in a manner which will be described in further detail presently.

The check valve 24 moves freely with respect to the armature 200 and does not necessarily move when the armature 200 is drawn toward diaphragm 160. At rest, the surface of check valve body 270 is held in contact with the edge of the valve formation 110 by the spring 240 acting upon the armature 200 which is then in contact with check valve body 270 and the compressed spring 276. When the armature 200 is drawn toward diaphragm 160, the force of spring 240 is no longer transferred to the check valve 24 and the force holding the surface of check valve body 270 against the valve formation 110 is decreased to that provided by spring 276, which generally provides a force less than that provided by spring 240. If armature 200 is drawn toward electromagnet 140 with sufficient velocity, pressure within the pump housing 12 between the end face 216 of plunger 204 and the check valve body 270 decreases to a level below the level at the pump inlet 18, and the net force due to fluid pressure from inlet 18 acting on the check valve 24 tends to move the surface of check valve body 270 away from contact with the end of the inlet fitting. If the net force due to the fluid pressure exceeds that provided by the spring 266, then check valve 24 moves away from the inlet fitting and fluid flows into the pump body. In fact, because the fluid is nearly incompressible the check valve 24 opens at approximately the same time that the armature 200 achieves enough velocity to force fluid out of the pump outlet 20. The forward pumping stroke of the armature 200 is completed when the armature pole face approaches contact with the diaphragm 160. When the armature velocity decreases to a level such that the displacement rate of the motion of the pole portion 202 no longer exceeds the leak rate between the outer surface of armature plunger 204 and surface 36 of the central interior passage of housing portion 30, the pressure within the pump housing 12 begins to increase. When the force due to the pressure difference across the check valve 24 no longer exceeds the force of spring 266, the check valve member 270 moves toward the valve formation 110 and prevents flow out of the inlet port 18 of the pump.

Thus, during the forward pumping stroke there is a reduction in the internal volume of the pump downstream of plunger 204, and there is a corresponding increase in the internal volume of the pump upstream of plunger 204. Accordingly, because the total internal volume of pump 10 does not change during a pumping stroke, fluid flows into inlet 18 and out of outlet 20 simultaneously with the forward motion of plunger 204. During the forward pumping stroke bypass check valve 86 is closed. Therefore, during the forward pumping stroke fluid flows in through pump inlet 18 to fill the increased internal volume upstream of plunger 204, and fluid flows out through pump outlet 20 to accommodate the decreased internal volume downstream of plunger 204. Thus, the internal volume of the pump on the downstream side of plunger 204 is a pumping chamber. The bypass circuit allows flow around plunger 204 during the plunger return stroke, while back flow is prevented by check valve 24.

When electrical excitation of coil 144 ceases, armature 200 is moved in the opposite direction, i.e. to the right as viewed in FIG. 1, by the force of biasing spring 240 until the armature reaches the rest position. During the return stroke the bypass check valve 86 is open with the result that the return motion of armature 200 is relatively rapid as previously described. During the return stroke of armature 200, check valve 24 is held against valve formation 110 primarily by the force of spring 276 supplemented by the difference between the outlet and inlet pressures acting on the check valve seat. When the return stroke is completed the spring force is increased to that of spring 240. The average pumping rate is determined by the rate of return of armature 200 to the rest position. Thus, the relatively rapid return of armature 200 provided by bypass check valve 86 increases the maximum available pumping rate. Armature 200 remains in the rest position with inlet 18 closed and waiting for the next forward pumping stroke which occurs when magnet 140 is energized again.

Thus, during the return stroke of armature 200, the check valve 24 is closed and bypass check valve 86 is open. The bypass circuit including the open check valve 86 allows flow around plunger 204 during the plunger return stroke, while backflow is prevented by check valve 24. The internal volume upstream of plunger 204 decreases, and excess fluid is removed from that volume through bypass check valve 86. The internal volume downstream of plunger 204 increases, and fluid is supplied to that increased volume by the flow of fluid through bypass check valve 86.

Figure 2:
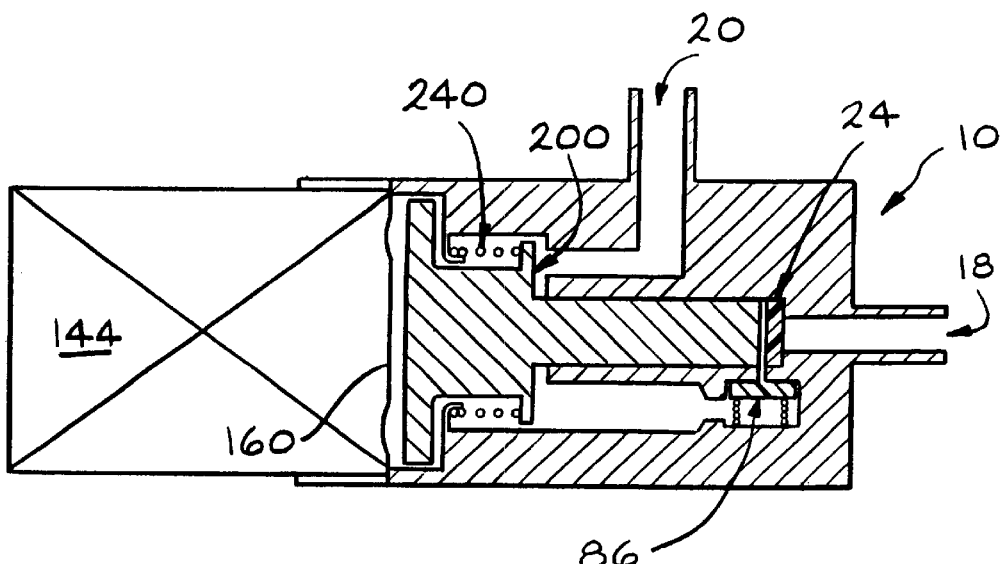
FIGS. 2–5 are diagrammatic views illustrating operation of the pump of FIG. 1.
Figure 3:
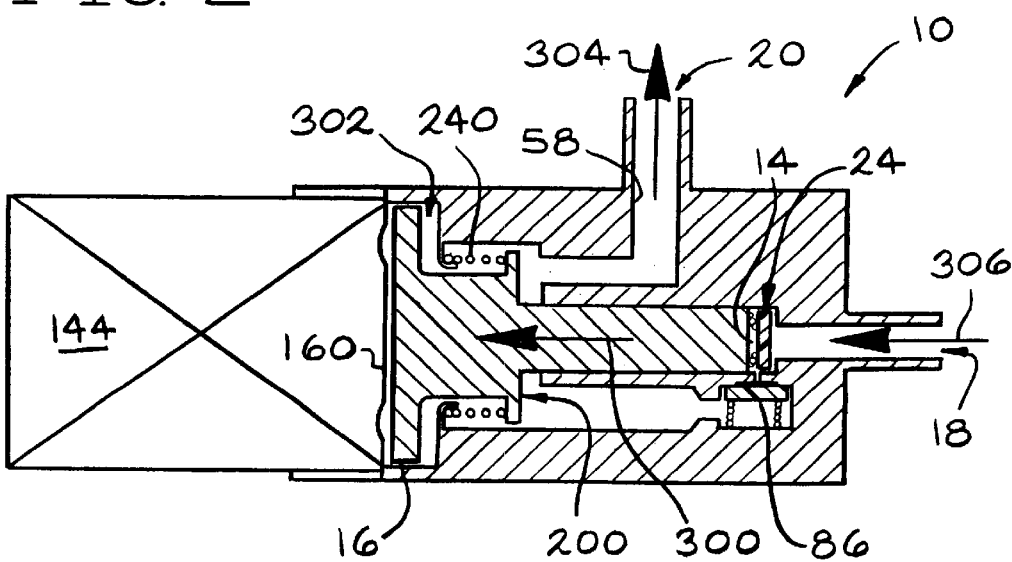

The foregoing operation of pump 10 is illustrated further in FIGS. 2–5. FIG. 2 shows the principal components of pump 10 in their respective locations at a stage between the forward and return strokes. FIG. 3 illustrates the forward pumping stroke where armature 200 moves in the forward direction of arrow 300, fluid flows out from output chamber 16 as indicated by arrow 302 and then from outlet 20 through conduit 58 as indicated by arrow 304, and fluid flows in through inlet 18 as indicated by arrow 306 past the unseated check valve 24 into the fluid receiving chamber 14. During the forward pumping stroke, bypass valve 86 is closed.

Figure 4:
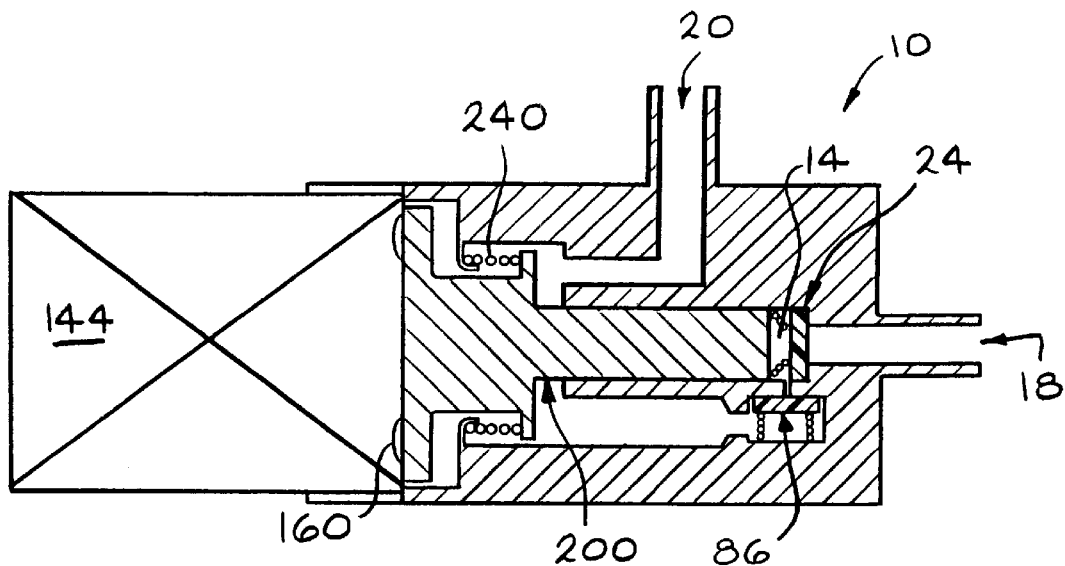
Figure 5:
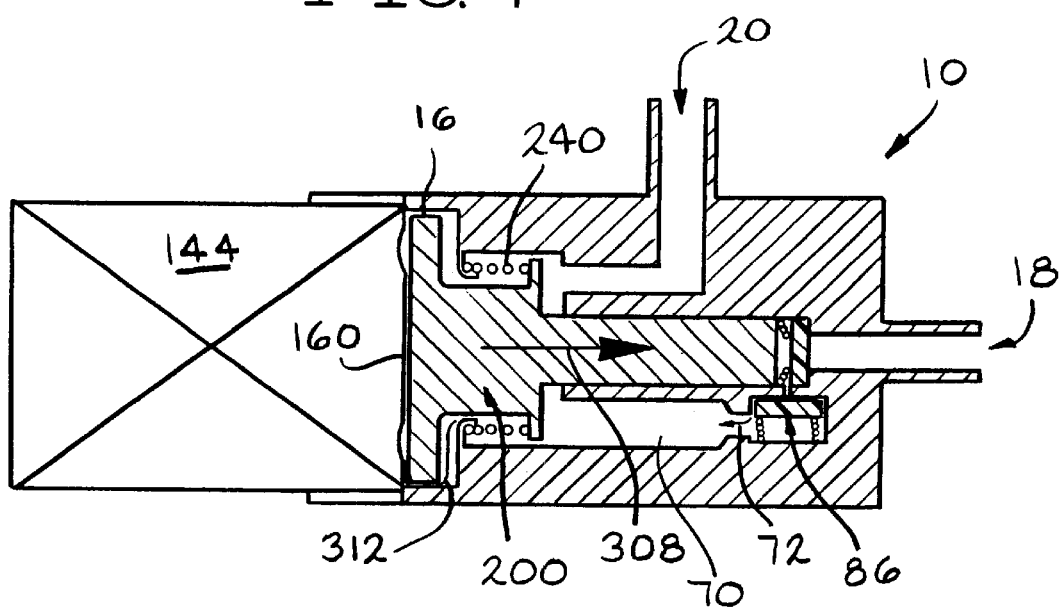

FIG. 4 shows the principal components of pump 10 in their respective locations at the completion of the forward pumping stroke. Armature 200 approaches contact with diaphragm 160, check valve 24 is closed and bypass check valve 86 is closed. The flow of fluid out from chamber 16 and out through outlet 20 is completed, and fluid has filled receiving chamber 14. FIG. 5 illustrates the return stroke where armature 200 moves in the direction of arrow 308, check valve 24 is closed and bypass check valve 86 is open. Fluid flows from receiving chamber 14 past the unseated check valve 86 into passages 72 and 70 as indicated by arrow 310 and then into output chamber 16 as indicated by arrow 312 in preparation for the next forward pumping stroke of armature 200.

Long term sealing is provided by the relatively stronger spring 240, and short term sealing while armature 200 is forward is provided by the relatively weaker spring 276. As a result, there can be satisfactory sealing against the back flow when the pump is not in operation, while the pressure drop across the check valve 24 during the pump stroke is small.

The relatively smaller diameter of armature plunger 204 as compared to pole portion 202 allows it to pump against higher back pressures without saturating the existing magnetic circuit. An additional advantage of this configuration is that for a given stroke volume, the smaller diameter of plunger 204 allows that the linear stroke be longer. This tends to improve the stability of the stroke volume since the effect of seat swelling or stroke volume is smaller. Another advantage arises from the fact that the volume of the pump chamber 14 with armature 200 in the rest position is smaller for the smaller combination of plunger 204 and the passage in housing portion 30.

The surface of barrier 160 facing armature 200 is provided with a slightly offset portion 316 extending toward or facing armature 200. The manner in which offset portion 316 is formed will be described further on in the specification. The degree of offset in the surface of barrier 160 is sufficient to change the behavior of the armature 200 during the return stroke thereof as compared to a completely flat or planar surface of barrier 160. In particular, the offset surface of barrier 160 is believed to reduce the pressure difference at the armature pole face which may occur if a gas-liquid interface should encircle the armature pole face surface in contact with barrier plate 160. Such a gas-liquid interface could otherwise support a pressure difference at the armature pole face sufficient to overcome the force of armature return spring thereby slowing or interfering with the return stroke of armature 200. Thus, the offset surface of barrier 160 serves to reduce the force which may under certain circumstances hold the armature pole face close to the barrier 160 in the presence of a liquid-gas interface. The offset surface of barrier 160 also serves to decrease the time required for the armature pole face to separate from the barrier 160 at the beginning of the plunger return stroke. This is a viscous flow effect and occurs even if no liquid gas interface is present.

There is a relatively small clearance between the outer surface of armature plunger portion 204 and the inner surface 36 of housing portion 30. As more stringent requirements are imposed on the accuracy of the pump pulse volume, smaller clearances become necessary and these in turn require better alignment of the plunger 204 and cylinder or surface 36 assemblies. The pump of the present invention provides a simplification by guiding the armature 200 entirely on a lengthened plunger 204 and cylinder 36. In other words, there is a clearance of relatively small width between armature plunger portion 204 and housing surface 36, and the length of plunger portion 204 is selected to provide the sole means for guiding movement of armature 200 within housing 30. The lengthened plunger 204 and cylinder 36 also tend to reduce the fluid leakage through the clearance between the plunger 204 and cylinder 36 and this allows somewhat greater clearance to be permitted between the plunger 204 and cylinder 36. As a result of these changes no alignment of either the plunger 204 or of the cylinder 36 related parts is required during assembly. The precision of the plunger 204 and cylinder 36 parts still must be high, however.

By way of example, in an illustrative pump, the length of armature plunger portion 204 measured from axial end face 216 to a plane containing housing wall 54 is about 0.21 inch. The diameter of plunger portion 204 is from about 0.07000 inch to about 0.07030 inch, and the diameter of passage 36 is from about 0.07040 inch to about 0.07055 inch.

The body of armature pole portion 202 is of the same material throughout, and surface 208 of the body is uniform and smooth over the entire extent thereof. The body of the armature pole portion 202 is formed of the chrome, molybdenum and iron alloy described above which has relatively low springback so that the crimping engagement between the annular flange 228 and plunger formation 220 is retained. Thus, the method of attachment between armature pole portion 202 and plunger portion 204 utilizing the crimped flange 228 on end face 210 of pole portion 202 leaves the opposite surface 208 of pole portion 202 smooth with no machining required during assembly. It does not insert any non-magnetic material into the magnetic circuit, and it provides a relatively more secure attachment by virtue of the relatively low springback of the above-mentioned alloy which is the outer material of the crimp.

In the assembly of return spring 240, retainers 244 and 250 and locking ring 254 on armature 200, after the armature pole and plunger portion 202 and 204, respectively, have been joined together by crimping flange 228 on formation 224 as previously described, the first retainer element 244 and return spring 240 are moved over along plunger portion 204 toward pole portion 202. Inner retainer 250 then is moved along plunger portion 240 and onto armature formation 220 where it fits within spring 240 and shoulder 248 engages the end of spring 240. Next, retainer 250 is moved axially toward pole portion 202 against the force of spring 240, locking ring 254 is installed and retainer 250 is released and locked in place as shown in FIG. 1.

Thus, in order to provide access to the assembly during manufacture of pump 10, the return spring 240 and spring retainer 244 have been designed to be removable. The inner spring retainer 250 is secured by locking ring 254 which engages both the plunger and the inner spring retainer. In order to remove the locking retainer it is necessary to move the inner spring retainer 250 toward the pole button 202 far enough so that the inner spring retainer 250 moves free of the locking ring 254. Dimensions are chosen such that when the assembly is installed in the pump the inner spring retainer 250 contacts the outer spring retainer 244 before the locking ring 254 is freed. Thus after the pump is assembled the locking ring 254 cannot be removed. Prior to assembly of the pump, however, the inner spring retainer 250 and the return spring 240 can easily be removed from or reinstalled on the plunger assembly.

In operation of a pump of the type disclosed herein, it is important to have assurance that the stroke volume delivered with the initial stroke setting will be close to the target volume. In pumps heretofore available, the foregoing has been achieved by assembling a pump, priming it and operating it for a given time, for example approximately 16 hours, measuring the delivered stroke volume and then inserting or removing a shim of appropriate size, repriming the pump and remeasuring the stroke volume. The basic reason for this is dimensional tolerance stack up. The physical dimensions of the parts which are involved in determining the geometric stroke and the diameters of the piston and cylinder which determine the amount of fluid leakage past the piston all contribute to the determination of the actual stroke volume delivered. A more efficient method for reaching the required shim configuration could save a significant amount of the time required to assemble a pump and it would allow the processing of more pumps with the available test equipment.

Figure 6:
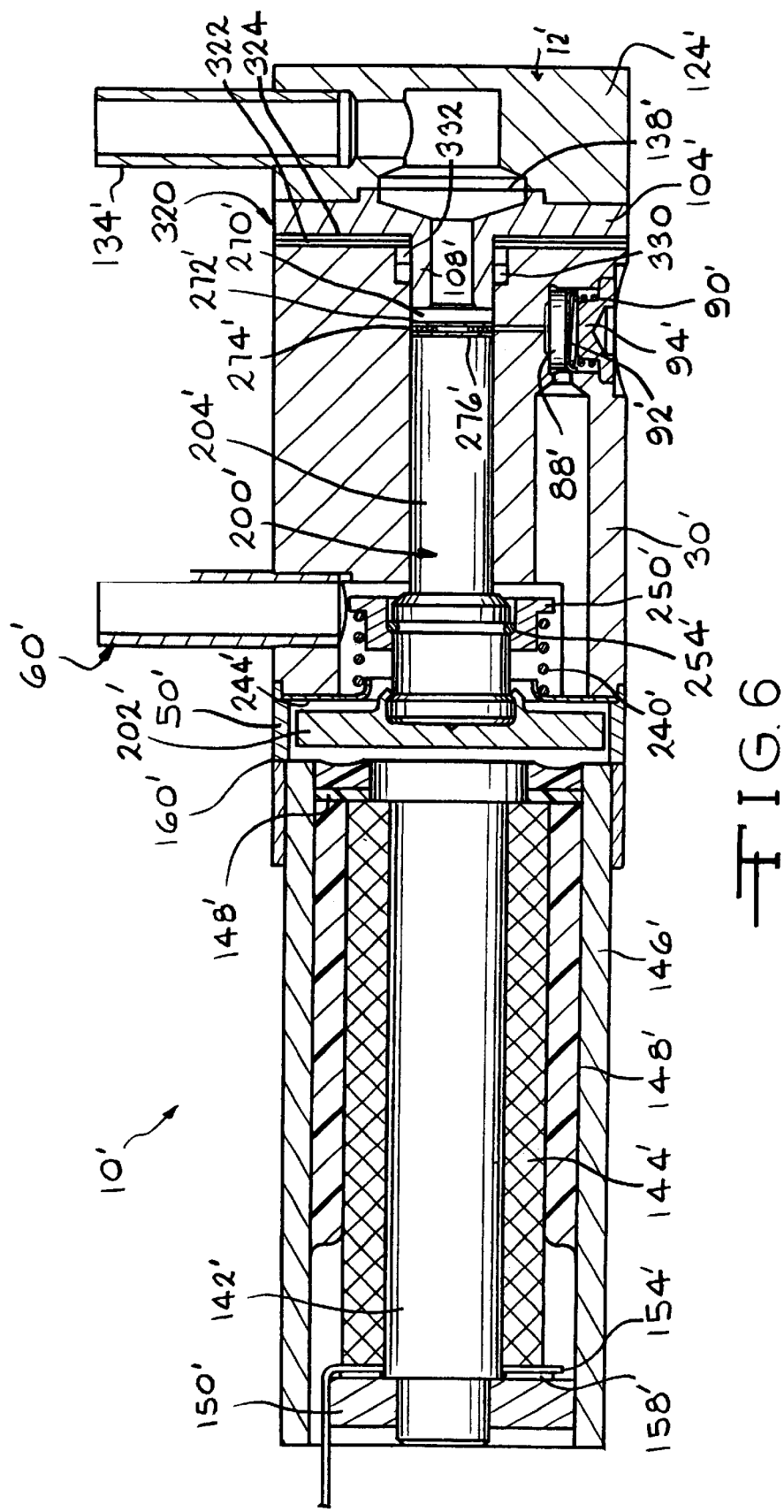
FIG. 6 is a fragmentary sectional view of a pump similar to the pump of FIG. 1 and provided with shims for adjusting the stroke volume.
Figure 8:
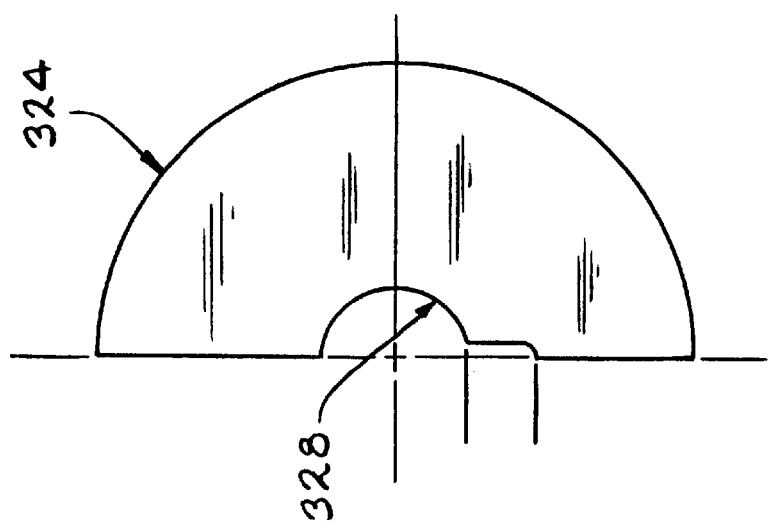
FIG. 8 is an elevational view of another of the shims in the pump of FIG. 6.
Figure 7:
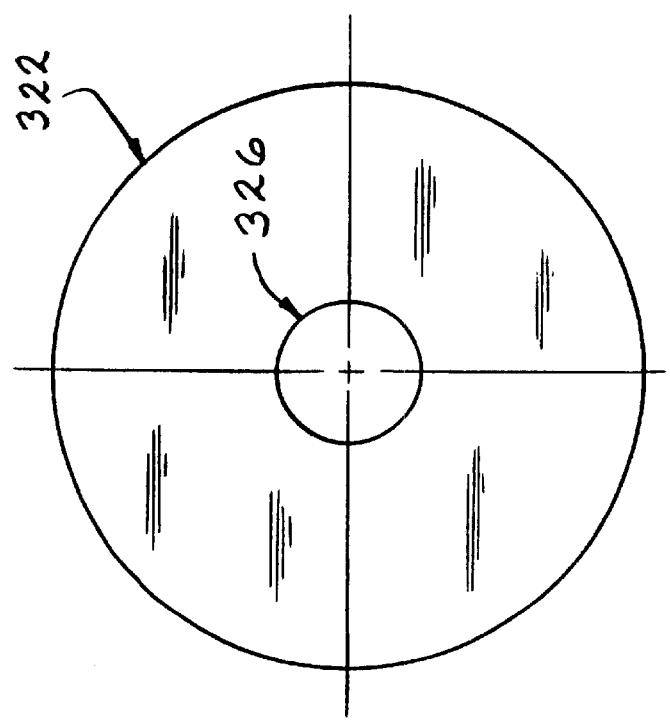
FIG. 7 is an elevational view of one of the shims in the pump of FIG. 6.

An approach to accomplishing this according to the present invention involves developing a shimming configuration which allows shims to be replaced without loss of prime. Referring to FIGS. 6–8, wherein components similar to those in the pump of FIG. 1 are identified by the same reference numerals provided with a prime designation, the armature 200' comprising pole portion 202' and plunger portion 204' is of fixed length and housing 12' includes the pair of components 30' and 104' having shim means generally designated 320 located therebetween so as to allow adjustment of he delivered stroke volume of armature 200'. Shim means 320 includes a solid shim element 322 permanently located between housing components 30' and 104', and one or more split shim elements 324 removably located between the housing components 30' and 104'. The solid shim element 322 is shown in FIG. 7 and is in the form of a disc having a central opening 326 of a diameter enabling it to be placed on the boss-like extension 108' of housing component 104'. The outer diameter of shim 322 is substantially equal to the outer diameter of housing components 30' and 104'. FIG. 8 illustrates one-half of a split shim element 324 which is in the form of half of a disc. The semi-circular recess 328 is of a dimension and shape enabling it to receive half the circumference of extension 108' of housing component 104'. Two such split shim elements 324 are provided on diametrically opposed portions of the extension 108'. If necessary, a number of such split shim elements 324 can be employed in axially adjacent relation in the assembly.

There is also provided fluid sealing means in the form of O-ring 330 operatively associated with shim means 320 to allow removal of components of the shim means 320 without loss of prime of pump 10. The O ring 330 is used to avoid leakage of air into the flow path as the seat ferrule 104 is moved relative to the pump housing component 30', and the split shims 324 are inserted from two sides of the pump. A potential problem with a configuration such as this is the possibility of motion of the O ring 330 during the pump stroke. This might change the pump stroke perhaps leading to random changes during the life of the pump. This problem has been addressed by including a compression ring 332 to confine the O ring to one end of its groove.

Thus, external shimming is introduced to adjust the stroke volume delivered by pump 10'. The objective accomplished with the external shimming is to shorten the time required to adjust the pump to its desired stroke volume by allowing insertion and removal of shims without the introduction of air into the flow path, and therefore without the need for repriming before the new stroke volume can be measured accurately.

The present invention addresses a potential problem with pump operation which may be a factor in increasing the level of damage to fragile drug molecules as they pass through the pump. The problem arises during the initial motion of the pump plunger 204. As the plunger first begins to move, the volume of the pump chamber (between the plunger face 210 and the check valve seat) begins to increase. During the initial motion, however, the check valve 24 remains closed until the compression of the rubber seat disk is relieved. The check valve 24 cannot open fully until the plunger 204 has traveled a significant distance.

At least during the peak of the capacitor discharge the magnetic force applied to the armature 200 is sufficient to drive the pressure in the pump chamber to vacuum. The dead end pressure capability is 20 psid. It is at least conceivable therefore that the fluid in the pump chamber may flash to vapor during the early part of the armature stroke in order to fill the volume vacated by the moving plunger. In addition, there must exist a very high shear situation in the fluid as the check valve first opens and fluid rushes in to fill the pump chamber. Either of these phenomena might be capable of damaging the drug. The situation would be much improved if the check valve were of larger diameter. Ideally the diameter of the sealing surface of the check valve should approach the diameter of the plunger. If so, during the initial part of the stroke, the relaxation of the check valve seat compression could itself be sufficient to make up the volume displaced by the moving armature. Flashing to vapor, if it exists in the present pump, might be eliminated by a larger diameter check valve, High shear during the first motion of the plunger 204 should also be reduced and together these effects may have a significant impact on the stability of the drug.

An improved check valve 340 is shown in FIGS. 9 and 10 wherein components similar to those in the pump of FIG. 1 are identified by the name reference numerals provided with a double prime designation. The improved check valve 340 is provided in an effort to improve the flow characteristics therethrough so as to reduce the damage to fragile drugs as they pass through pump 10. Check valve 340 includes a body portion 342 and a stem portion 344. A valve seat 346 of suitable resilient material is located in a central axial recess formed in the end of housing body portion 30". Seat 346 is held in place by a ferrule member 350 having a central, hub-like extension which fits in the recess in housing portion 30" and contacts the surface of seat 346. The check valve stem portion 344 extends axially through ferrule 350 and carries a biasing spring assembly. In particular, a coil spring 354 in coaxial relation to stem 344 has one end abutting a surface of ferrule 350 and the opposite end contacting a spring retainer assembly 356 on the end of stem 344. Retainer assembly 356 comprises a pin 358 extending through stem 344 and a pair of inverted cup-shaped retainers 360, 362 provided with central apertures to receive stem 344. Spring 354 seats in one of the retainers and pin 358 is received in the other. An annular retaining element 370 received in body 124" surrounds assembly 356 and supports a disc filter 372.

Check valve 340 is shown in further detail in FIG. 10. A through bore or aperture 374 is provided near the end of stem portion 344 to receive pin 358. An annular recess 376 is formed at the junction between body portion 342 and stem portion 344. An annular sealing surface 378 is defined between the outer periphery of recess 376 and the annular peripheral surface 380 of body portion 342. The opposite axial end face 382 of body portion 342 faces toward armature end face 216". Providing annular recess 376 results in displacing the check valve sealing surface 378 radially outwardly. In other words, the check valve structure of FIGS. 9 and 10 results in a significantly larger diameter sealing surface as compared to that of the check valve in FIG. 1. By way of example, sealing surface 378 has a diameter of about 0.06 inch as compared to a 0.04 inch diameter sealing surface in check valve arrangements like those shown in FIG. 1. Viewing the foregoing in a different manner, the cross sectional area of the armature plunger portion is more than three times larger than the check valve area in arrangements of the type shown in FIG. 1. In the check valve arrangement of FIGS. 9 and 10 the armature plunger portion is only about 36 percent larger than the area of the check valve sealing surface 378. It is believed that the check valve arrangement of FIGS. 9 and 10 will apply significantly less stress to drugs being pumped.

The wear characteristics of the type of pump shown in FIG. 1 is satisfactory while the pump is pumping fluids. If the pump is operated dry and particularly if it is operated dry under vacuum the wear may be more serious. The problem is believed to occur when the pump is operated under conditions such that the oxide layer on the titanium, worn during a stroke, does not rebuild itself between strokes. It is possible that coating the plunger 204 or cylinder 36 or both with some hard material may prevent this wear. There is some experimental evidence that diamond-like nanocomposite material reduces friction and wear of titanium 6A14V or like material. For more information on the foregoing reference may be made to "Diamond-like Nanocomposites (DLN)" by V. F. Dorfman, *Thin Solid Films*, 212(1992) 267–273. The diamond-like nanocomposite material is within the category of amorphous hydrogenated carbon material. It is believed also that good results may be achieved even if only one surface of the wear couple is coated. Since the diamond-like nanocomposite coating process, like many of the coating procedures which might be considered for this purpose, is a line of sight deposition process, it is feasible to coat the outer surface of plunger 204 rather than surface of cylinder 36. An example of coating material is that commercially available from Advanced Refactory Technologies, Inc. of Buffalo, New York under the registered trademark Dylyn.

Other surface treatments or coatings also can be employed, for example ion implantation. Carbon, nitrogen or oxygen ions would appear to provide satisfactory results. For more information on treatment of titanium surfaces by ion implantation to increase wear resistance, reference may be made to "Friction and Wear of Titanium Alloys", F. M. Kustas and M. S. Misra, *ASM Handbook*, Vol. 18, 1992, pgs. 779–783.

It is possible also that coating surfaces within the pump other than those subject to mechanical wear may also result in some benefit. It is possible, for example, that a coating such as diamond-like nanocomposite may improve the compatibility of a surface with the drug passing through the pump. The seat ferrule 104, which cyclically contacts the rubber seat disk 270 via formation 110, would benefit if the tendency of degraded insulin to deposit on the seat ferrule surface were to be reduced by the coating.

A coating, generally designated 390 in FIG. 1, is on the outer surface of armature plunger 204 and is representative of the amorphous hydrogenated carbon coating or ion implantation surface treatment according to the foregoing description. The coating 390 on plunger 204 reduces its friction as it moves within the cylinder 36 and reduces the possibility of excessive wear in the event plunger 204 is cycled dry without the lubrication normally provided by the pumped fluid.

FIGS. 11–13 illustrate an armature pole portion 400 according to another embodiment of the present invention. Like pole portion 202 of FIGS. 1–5, pole portion 400 comprises a body in the general form of a disc having a first axial end face 402 which faces toward the barrier means 160 (not shown in FIGS. 11–13) and a second, opposite axial end face 404 which faces toward inlet port 18 (not shown in FIGS. 11–13). Pole portion 400 is of the same material as pole portion 202. End face 404 of pole portion 400 is provided with a recess 406 bordered by an annular peripheral flange 408 to receive the end of the armature plunger portion (not shown in FIGS. 11–13) in a manner similar to that of the embodiment of FIGS. 1–5.

The armature pole portion 400 of this embodiment is provided with at least one passage means therethrough and in the present illustration four axially extending through bores or passages 410, 412, 414 and 416 are shown. The passages 410–416 extend through the entire axial length of armature body 400 between the axial end faces 402 and 404. A plurality of radially disposed recesses 420, 422, 424 and 426 are provided in end face 402 and in communication with passages 410, 412, 414 and 416, respectively. Each recess 420–426 extends to the outer periphery of body 400. The passage means 410, 412, 414 and 416 serve to reduce the time required for armature pole portion 400 to separate from the barrier means 160 during movement of the armature toward the inlet port 18 and to reduce surface tension effects between the barrier means 160 and pole portion 400. The path for fluid flow defined by passage means 410, 412, 414 and 416 provides the foregoing results when energization of the electromagnet 130 (not shown in FIGS. 11–13) ceases and the force of spring 240 (not shown in FIGS. 11–13) begins to move armature pole portion 400 away from the barrier means. Initial fluid flow into passages 410, 412, 414 and 416 is enhanced by the recesses 420, 422, 424 and 426. In addition, the foregoing is enhanced by the central conical formation or the barrier means 160 as previously described.

Simplification of the coil assembly procedure used to manufacture the pump 10 of the present invention is a significant improvement. In prior art pumps the assembly process can include a lengthy series of time consuming steps in which the spindle having been previously wound with a coil is inserted into the diaphragm end of the coil case and then potted with epoxy. The potted coil and case must then be machined precisely to the shape of a very blunt cone and epoxied to the diaphragm weld ring assembly. It is important that the epoxy which backs the diaphragm provide good support for the diaphragm since the diaphragm itself is not strong enough to resist the cyclic pressures generated within the pump. Achieving this is difficult. Multiple repotting steps are sometimes necessary. Vacuum potting reduces the number of potting steps but the apparatus used can be complicated and require extensive cleaning after each potting cycle. It is also important that the shape of the diaphragm after bonding of the coil face not be completely flat (assuming that the surface of the pole button which comes in contact with the diaphragm is flat). If both the pole button and the diaphragm were flat then the plunger would tend to return to its rest position slowly because of viscous effects, and if an air-liquid interface were present there would be some risk that the plunger might not return at all. It is also necessary that these surfaces not deviate excessively from flatness since imperfect mating of the two surfaces increases the gap in the magnetic circuit and decreases the efficiency of the solenoid. Thus the shapes of the coil face and diaphragm must be controlled carefully. In prior art pumps the pole button has been lapped flat and the shape of the diaphragm controlled by machining the face of the assembled and potted coil and case before the diaphragm is attached. This machining interrupts the manufacturing process and can represent an expensive step in assembly.

Briefly, the simplified coil assembly process is as follows. The coil case 146 is cylindrical without a crimp at the lead end so that the subassembly of coil 144 on spool 142 may be inserted from the end opposite the diaphragm 160. This allows the bonding of the diaphragm to the coil face and the potting of the coil within the case to occur simultaneously. Initially the diaphragm-weld ring 50, 162 assembly is placed on a fixture which is shaped in a manner such that when the diaphragm is forced down upon it the diaphragm is deformed so that the edge of the diaphragm is elevated 0.001" to 0.002" above its center. The fixture will be shown and described in detail presently. The lower outside surface of the coil case 146 is coated with epoxy to ensure that the case will bond to the weld ring 162 and the coil case is then placed upon the diaphragm assembly and held down in a suitable manner. The coil case is then partially filled with epoxy to a level which has been determined to be sufficient to ensure that the coil case will be nearly filled after insertion of the spindle and coil. The spindle, coil, and coil washer 150, 158 assembly is then placed within the case and held down by a spring loaded arm in a manner which will be described. Relatively simple apparatus is adequate, the coil case becomes a simpler part, and the machining step is eliminated. The assembly process advantageously is relatively quick.

FIGS. 14–19 show a preferred form of fixture assembly 440 for carrying out the foregoing method. Fixture 440 comprises a solid rectangular base 442 including a series of through bores 444 each containing a rod-like ram 446 which fits closely but axially movably within its corresponding bore 444. Each ram 446 has one end 448 projecting beyond a top surface 450 of fixture base 442 as shown in FIGS. 14 and 15. The opposite end 452 of each ram 446 is engaged by a set screw 454 threaded in the end of each bore 444 adjacent the opposite or bottom surface 456 of fixture base 442. During use of fixture assembly 440, base 442 can be held in a clamp or other suitable supporting means (not shown) permitting access to the regions adjacent the opposite surfaces 450 and 456 of base 442.

Fixture assembly 440 further comprises a top clamp number 460 in the form of an elongated rectangular bar or strip which is shown in further detail in FIGS. 16 and 17. In the arrangement shown, member 460 is of substantially the same length and width as top surface 450 of fixture base 442. Member 460 has oppositely disposed surfaces 462 and 464, the latter facing toward fixture top surface 450. Member 460 is provided with a first series of spaced-apart circular openings 466 each of a diameter to receive closely but removably one end of an outer case of a corresponding coil assembly in a manner which will be described. Each opening 466 is formed to include an annular shoulder 468 adjacent surface 462 for a purpose which will be described. Member 460 also is provided with a second series of spaced-apart circular openings 470 to receive shoulder screws 472 for connecting member 460 to fixture base 442. The openings 466 and 470 are in alternating spaced relation along the length of member 460. Each shoulder screw 472 has a head 474 at one end which engages surface 462 of member 460. The shoulder screws 472 have threaded opposite ends 476 which are connected in threaded bores 478 provided in surface 456 of fixture base 442.

Fixture assembly 440 further comprises clamping means 484 carried by member 460 and provided with each of the openings 466 so as to be operatively associated with each of the coil case assemblies in a manner which will be described. Each clamping means 484 comprises a substantially U-shaped leaf spring element having a web or central portion 486 and a pair of arm portions 488 and 490 extending therefrom. Web portion 486 is provided with an opening 492 to receive a button element 494 for a purpose to be described. Arm portions 488 and 490 have openings 496 and 498 which receive pins 500 and 502, respectively, which fit into openings 504 and 506, respectively, in bar member 460 for connecting spring 484 to member 460.

The method is carried out using fixture assembly 440 in the following manner. The base assembly 442 of the gluing/potting fixture 440 is pre-assembled using base 442, rams 446 and set screws 454. Each ram 446 is positioned by its set screw 454 so that the coil assembly being glued will be just above the surface 450 of base 442 when the coil assembly is placed on the end of the ram 446. Then a plurality of barrier assemblies is provided each including diaphragm 160 and weld rings 50 and 162 fixed thereto, one of which barrier assemblies is shown in FIG. 20. Potting compound such as epoxy is applied to the inner surface 510 of weld ring 162. Then one end of coil assembly case 146 is placed in weld ring 162, being installed in a twisting motion to distribute the potting compound. Alternatively, the outer surface of the end of casing 146 can have the epoxy applied thereto. Case 146 has an outer diameter enabling it to be received firmly in weld ring 162. Then the combination of case 146, weld rings 50, 162 and diaphragm 160 is placed on the end 448 of ram 446. The foregoing is repeated for each of the rams 446 in fixture assembly 440. As a result, each case 146 and barrier assembly 160, 50 and 162 is supported so that each case 146 is disposed generally vertically with the open end thereof facing generally upward.

Next, top clamp member 460 is positioned over the open ends of cases 146 so that the annular shoulders 468 of the openings 466 abut the axial end faces of the corresponding cases 146 as shown in FIG. 14. Clamp member 460 is secured in place by means of shoulder screws 472. Then set screws 454 are advanced to move rams 446 upwardly to secure each case 146 and associated barrier assembly in place.

A plurality of electromagnet assemblies each comprising coil 144 on spool 142 is provided. A centering spacer 520 shown in FIG. 21 is placed in each casing 146 so as to rest on the surface of diaphragm 160. Spacer 520 has a central opening 522 of a diameter to receive the end of spool 142. The flat major edges 524 of spacer 520 are joined by four minor edges 526 which lie on an imaginary circle 528 having a diameter such that spacer 520 fits in case 146. Next, potting compound such as epoxy is introduced into the interior of each case 146 in an amount determined to fill a substantial portion of the portion of the space within the interior of case 146 after insertion of the electromagnet assembly. The potting compound itself holds coil 144 from moving in response to pressure acting on diaphragm 160 during operation of the completed pump 10 so that the interior of case 146 must be provided with enough epoxy during this step of the method to satisfy this requirement. The space between flats 524 of spacer 520 and the inner surface of case 146 accommodates flow of the potting compound.

Next, each electromagnet assembly comprising coil 144 on spool 142 is inserted into a corresponding case 146 and so that the end of spool 142 fits into the opening 522 of spacer 520. As the electromagnet assembly is inserted into case 146 potting compound is displaced into the space between coil 144 and the inner wall of case 146. Then a spring clamp 484 is installed on each assembly to apply clamping force to hold the electromagnetic assembly in place. In particular, for each assembly, the leaf spring element shown in FIGS. 18 and 19 with button 494 received an opening 492 of web portion 486 is positioned so that the end of button 494 contacts the end of spool 142 as shown in FIG. 15. Pins 500 and 502 carried by arm portions 488 and 490 are inserted into openings 504 and 506, respectively, in bar member 460 so that spring 484 is connected to member 460 to apply clamping force to the electromagnet assembly.

The final step in the foregoing method is curing the potting compound in casing 146. This is done by placing the loaded fixture assembly 440 into an oven preheated to 57° C. and curing for a minimum of 15 hours. During the curing cycle the spring clamps 484 apply steady clamping force to each of the electromagnet assemblies. After the curing cycle is completed, spring clamps 484 are disconnected from bar member 460 which in turn is disconnected from fixture base 442 by removing shoulder screws 472 so that the completed electromagnet assemblies can be removed. The completed assemblies then are combined with the remainder of the pump components including housing 12, check valve 24, armature 200, bypass valve 86 and the other components previously described.

While the foregoing method advantageously avoids the crimping of coil case 146 at the lead end, in situations where such crimping of case 146 is desirable or necessary, fixture 440 can accommodate the same. FIG. 20 illustrates in detail the upper surface 530 of each ram 446 which surface has a shallow central recess 532 which forms the offset portion 316 of diaphragm 160 when the components of fixture assembly 440 are connected together to apply pressure to the electromagnet assembly. The shape of offset portion 316 is determined by the shape of recess 532. Accordingly, instead of being flat, portion 316 can be slightly conical simply by altering the shape of recess 532. In addition, it is within the scope of this invention to alternatively shape the end face 208 of armature pole portion 202 by machining to have a central, flat offset portion or a slightly conical portion to enhance separation of barrier 160 and pole portion 202 during the return stroke of armature 200 as previously.

It is therefore apparent that the present invention accomplishes its intended objects. While embodiments of the present invention have been described in detail, that has been done for the purpose of illustration, not limitation.

What is claimed is:

1. An electromagnetic pump comprising:
  a) a housing having an interior fluid containing region including a fluid receiving chamber and a fluid output chamber in fluid communication therewith, an inlet in fluid communication with said receiving chamber and an outlet in fluid communication with said output chamber;
  b) check valve means operatively associated with said fluid containing region for allowing fluid flow in a direction from said inlet through said outlet and blocking fluid flow in a direction from said outlet through said inlet;
  c) electromagnet means carried by said housing and located external to said fluid containing region;
  d) an armature positioned in said fluid containing region of said housing having a pole portion located for magnetic attraction by said electromagnet means and having a plunger portion rigidly extending from said pole portion, said plunger portion having one end adjacent said pole portion and an opposite end and having a constant cross-sectional dimension between said ends, said armature being movably supported in said housing for movement from a rest position through a forward pumping stroke when attracted by said electromagnet means to force fluid from said output chamber through said outlet and for movement in an opposite direction through a return stroke back to said rest position, said armature pole portion having a cross-sectional dimension measured in a direction substantially perpendicular to the direction of movement of said armature at least two times greater than a cross-sectional dimension of said armature plunger portion, there being a clearance of relatively small width between said armature plunger portion and said housing extending along the entire length of the constant cross-sectional dimension of said armature plunger portion between both of said ends, the width and length of said clearance and the length of the constant cross-sectional dimension of said plunger portion between said ends being selected to provide the sole means for guiding movement of said armature in said housing and the length of the constant cross-sectional dimension of said plunger portion between said ends being selected to restrict the amount of fluid leakage through said clearance thereby relaxing requirements imposed on the width of said clearance;
  e) means defining a magnetic circuit including said electromagnet means and said armature and a gap between said pole portion of said armature and said electromagnet means for moving said armature toward said electromagnet means to close said gap in response to electrical energization of said electromagnet means; and
  f) controlled means for providing a path in said housing for fluid around said armature plunger portion from said fluid receiving chamber to said fluid output chamber only during said return stroke of said armature.

2. An electromagnetic pump comprising:
  a) a housing having an interior fluid containing region including a fluid receiving chamber and a fluid output chamber in fluid communication therewith, an inlet in fluid communication with said receiving chamber and an outlet in fluid communication with said output chamber, said inlet having a cross-sectional dimension and said fluid receiving chamber having a cross-sectional dimension greater than that of said inlet;

b) check valve means operatively associated with said fluid containing region for allowing fluid flow in a direction from said inlet through said outlet and blocking fluid flow in a direction from said outlet through said inlet, said check valve means including means defining a valve seat surface adjacent a junction between said inlet and said fluid receiving chamber;

c) electromagnet means carried by said housing and located external to said fluid containing region;

d) an armature positioned in said fluid containing region of said housing having a pole portion located for magnetic attraction by said electromagnet means and having a plunger portion extending from side pole portion, said armature being movably supported in said housing for movement from a rest position through a forward pumping stroke when attracted by said electromagnet means to force fluid from said output chamber through said outlet and for movement in an opposite direction through a return stroke back to said rest position, there being a relatively small clearance between said armature plunger portion and said housing;

e) means defining a magnetic circuit including said electromagnet means and said armature and a gap between said pole portion of said armature and said electromagnet means for moving said armature toward said electromagnet means to close said gap in response to electrical energization of said electromagnet means;

f) controlled means for providing a path in said housing for fluid around said armature plunger portion from said fluid receiving chamber to said fluid output chamber only during said return stroke of said armature; and g) said check valve means comprising a valve element and biasing means, said biasing means being located in said inlet and said valve element having a body portion located in said fluid receiving chamber and a stem portion extending from said body portion into said inlet for operative connection to said biasing means, said body portion having a sealing surface dimensioned relative to the cross-section of said plunger to reduce vapor flashing and shearing of fluid between said check valve element and said plunger during the forward pumping stroke of said armature, said sealing surface being annular and having an inner diameter located radially outwardly of the junction between said inlet and said fluid receiving chamber.

3. A pump according to claim 2, wherein the sealing surface of the valve element is defined by an annular recess at a junction between the valve element body portion and the valve element stem portion.

4. A pump according to claim 3, wherein the sealing surface of the valve element is defined between the outer periphery of the annular recess and an annular peripheral surface of the valve element body portion.

5. A pump according to claim 4, wherein the annular peripheral surface of the valve element body portion has a diameter substantially equal to the diameter of the armature plunger portion.

6. A low power electromagnetic pump for medical use in delivering fluid to the body of a patient and comprising:

a) a housing having an interior fluid containing region including a fluid receiving chamber and a fluid output chamber in fluid communication therewith, an inlet in fluid communication with said receiving chamber and an outlet in fluid communication with said output chamber;

b) check valve means operatively associated with said fluid containing region for allowing fluid flow in a direction from said inlet through said outlet and blocking fluid flow in a direction from said outlet through said inlet;

c) electromagnet means carried by said housing and located external to said fluid containing region;

d) an armature positioned in said fluid containing region of said housing having a pole portion located for magnetic attraction by said electromagnet means and having a plunger portion extending from said pole portion, said armature being movably supported in said housing for movement from a rest position through a forward pumping stroke when attracted by said electromagnet means to force fluid from said output chamber through said outlet and for movement in an opposite direction through a return stroke back to said rest position, there being a relatively small clearance between said armature plunger portion and said housing, said armature plunger portion being of a material on which a surface oxide layer forms;

e) means defining a magnetic circuit including said electromagnet means and said armature and a gap between said pole portion of said armature and said electromagnet means for moving said armature toward said electromagnet means to close said gap in response to electrical energization of said electromagnet means;

f) controlled means for providing a path in said housing for fluid around said armature plunger portion from said fluid receiving chamber to said fluid output chamber only during said return stroke of said armature; and g) a wear resistant coating of amorphous hydrogenated carbon on said armature plunger portion to compensate for said oxide layer being worn and not rebuilt during strokes of said armature and to reduce any excessive wear if the armature is cycled dry without lubrication provided by pumped fluid.

7. A pump according to claim 6, wherein said armature plunger portion is of titanium.

8. A low power electromagnetic pump for medical use in delivering fluid to the body of a patient and comprising:

a) a housing having an interior fluid containing region including a fluid receiving chamber and a fluid output chamber in fluid communication therewith, an inlet in fluid communication with said receiving chamber and an outlet in fluid communication with said output chamber;

b) check valve means operatively associated with said fluid containing region for allowing fluid flow in a direction from said inlet through said outlet and blocking fluid flow in a direction from said outlet through said inlet;

c) electromagnet means carried by said housing and located external to said fluid containing region;

d) an armature positioned in said fluid containing region of said housing having a pole portion located for magnetic attraction by said electromagnet means and having a plunger portion extending from said pole portion, said armature being movably supported in said housing for movement from a rest position through a forward pumping stroke when attracted by said electromagnet means to force fluid from said output chamber through said outlet and for movement in an opposite direction through a return stroke back to said rest position, there being a relatively small clearance between said armature plunger portion and said housing, said armature plunger portion being of a material on which a surface oxide layer forms;

e) means defining a magnetic circuit including said electromagnet means and said armature and a gap between said pole portion of said armature and said electromagnet means for moving said armature toward said electromagnet means to close said gap in response to electrical energization of said electromagnet means;

f) controlled means for providing a path in said housing for fluid around said armature plunger portion from said fluid receiving chamber to said fluid output chamber only during said return stroke of said armature; and g) said armature plunger portion having an outer surface implanted with ions selected from the group consisting of carbon, nitrogen and oxygen ions for increasing the wear resistance of said surface to compensate for said oxide layer being worn and not rebuilt during strokes of said armature and to reduce any excessive wear if the armature is cycled dry without lubrication provided by pumped fluid.

9. A pump according to claim 8, wherein said armature plunger portion is of titanium.

* * * * *